(12) United States Patent
Dakka et al.

(10) Patent No.: US 7,649,100 B1
(45) Date of Patent: Jan. 19, 2010

(54) OXIDATION PROCESS IN THE PRESENCE OF CARBON DIOXIDE

(75) Inventors: Jihad M. Dakka, Whitehouse Station, NJ (US); Hans K T Goris, Laakdal (BE); Georges M. K. Mathys, Bierbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/719,375

(22) PCT Filed: Jun. 8, 1999

(86) PCT No.: PCT/EP99/03998

§ 371 (c)(1),
(2), (4) Date: Mar. 8, 2002

(87) PCT Pub. No.: WO99/64376

PCT Pub. Date: Dec. 16, 1999

(30) Foreign Application Priority Data

Jun. 8, 1998 (GB) .................................. 9812235.1

(51) Int. Cl.
*C07D 303/04* (2006.01)
(52) U.S. Cl. ..................................................... 549/513
(58) Field of Classification Search .................. 568/14; 549/513
See application file for complete search history.

(56) References Cited

U.S. PATENT DOCUMENTS

| 4,483,996 | A | 11/1984 | Jacobson |
| 4,824,976 | A | 4/1989 | Clerici et al. |
| 4,833,260 | A | 5/1989 | Neri et al. |
| 5,210,336 | A | 5/1993 | Gaffney et al. |
| 5,525,563 | A | 6/1996 | Thiele et al. |
| 5,591,875 | A | 1/1997 | Chang et al. |
| 5,646,314 | A | 7/1997 | Crocco et al. |
| 5,675,026 | A | 10/1997 | Thiele |
| 5,741,749 | A | 4/1998 | Crocco et al. |
| 5,916,835 | A | 6/1999 | Carroll et al. |
| 6,063,941 | A | 5/2000 | Gilbeau |
| 6,066,750 | A | 5/2000 | Chang |
| 6,169,050 | B1 | 1/2001 | Catinat et al. |
| 6,380,119 | B1 | 4/2002 | Grosch et al. |

FOREIGN PATENT DOCUMENTS

| DE | 19725820 | 12/1998 |
| EP | 0 385 631 | 9/1990 |

OTHER PUBLICATIONS

Thiele, et al.; Propylene Epoxidation with Hydrogen Peroxide and Titanium Silicalite Catalyst: Activity, Deactivation and Regeneration of the Catalyst; Journal of Molecular Catalysis A: Chemical, 1997, vol. 117, pp. 351-356.

*Primary Examiner*—Rebecca L Anderson

(57) ABSTRACT

The selectivity of an olefin epoxidation process catalyzed by a heterogeneous catalyst for example titanium silicalite is improved by performing the epoxidation in the presence of carbon dioxide. The catalysts used do not require regeneration on each recycle.

39 Claims, 5 Drawing Sheets

OXIDATION PROCESS IN THE PRESENCE OF CARBON DIOXIDE

CROSS-REFERENCE TO RELATED APPLICATIONS

The present application is a U.S. National Stage Patent Application of PCT application PCT/EP 99/03998, filed Jun. 8, 1999, which claims priority to Great Britain application GB 98122.35.1, filed Jun. 8, 1998. Both of these applications are fully incorporated by reference herein.

BACKGROUND OF THE INVENTION

The present invention relates to an oxidation process and in particular to a process for the oxidation of unsaturated hydrocarbons in the presence of catalyst under heterogeneous conditions.

It is well known that the epoxidation of unsaturated hydrocarbons e.g. olefinic compounds, with various oxidants such as hydrogen peroxide may be effectively catalyzed by certain synthetic zeolites containing metal atoms such as titanium atoms (see, for example, U.S. Pat. No. 4,833,260).

Various process modifications have been proposed to improve the conversion and selectivity of these oxidation reactions. U.S. Pat. No. 4,824,976 proposes that the non-selective ring-opening reactions which take place when epoxidation is performed in a protic medium such as water or alcohol may be suppressed by treating the catalyst prior to the reaction or during the reaction with a suitable acid neutralising agent. The neutralising agent is said to neutralise acid groups on the catalyst surface which tend to promote by-product formation U.S. Pat. No. 5,675,026 proposes the addition of neutral- or acid-reactive salts to the catalyst before or during the reaction to improve catalyst activity. U.S. Pat. No. 4,483,996 discloses a process for the conversion of olefins to olefin oxides and ketones. The process utilises a thallous catalyst, with molecular oxygen as oxidant in an aqueous carbon dioxide solvent. U.S. Pat. No. 5,591,875 proposes an epoxidation process which utilises a chelating agent to reduce the catalysts tendency to non-selectively decompose the hydrogen peroxide oxidant used. EP 0 385 631 A1 describes an oxidation process for the conversion of olefins to glycols utilising oxygen and carbon dioxide as reactants under supercritical conditions. A heterogeneous copper containing catalyst is proposed. U.S. Pat. No. 5,646,314 proposes performing the oxidation reaction in the presence of nonbasic salts in order to improve selectivity.

Furthermore it has long been recognised that metal containing zeolite catalysts rapidly become deactivated in use. There have been a number of methods developed to counter this deactivation and/or to regenerate the catalyst after use. U.S. Pat. No. 5,741,749 proposes a the regeneration of a titanium containing molecular sieve oxidation catalyst by treatment with a gas stream comprising specific amounts of molecular oxygen. WO 98/18555 proposes the regeneration of a titanium silicalite catalyst with a liquid solution of an oxidising agent. WO 98/18556 proposes the regeneration of a titanium silicalite catalyst under a specific gas flow In U.S. Pat. No. 5,210,336 a process is described for the conversion of olefins to glycols utilising a CuI/Cu$_2$O catalyst. The reaction is undertaken in the presence of carbon dioxide which acts as a solvent and a co-reactant, under supercritical conditions.

There are a number of problems with the processes of the prior art. Conversions and selectivities for the various reactions are in general still low or require additional process modifications which incur additional costs. Frequently the catalyst systems utilised require special treatments and/or frequent regeneration in order to maintain catalyst activity.

BRIEF SUMMARY OF THE INVENTION

It has been surprisingly found that the conversion and selectivity of oxidation processes, in particular the conversion of unsaturated hydrocarbons, especially olefins, to oxidation products especially oxirane compounds, are significantly improved by utilising a specific group of catalysts in the presence of carbon dioxide. It has also been surprisingly found that the heterogeneous catalysts of the present process maintain their activity for significantly longer periods of time and through many recycles through the process. This improved activity with respect to the catalyst means that costly and laborious pre-treatments and/or regenerations of the catalyst are either not required or are required at less frequent intervals in the process of the present invention compared to prior art processes.

DETAILED DESCRIPTION OF THE INVENTION

Figure 1:
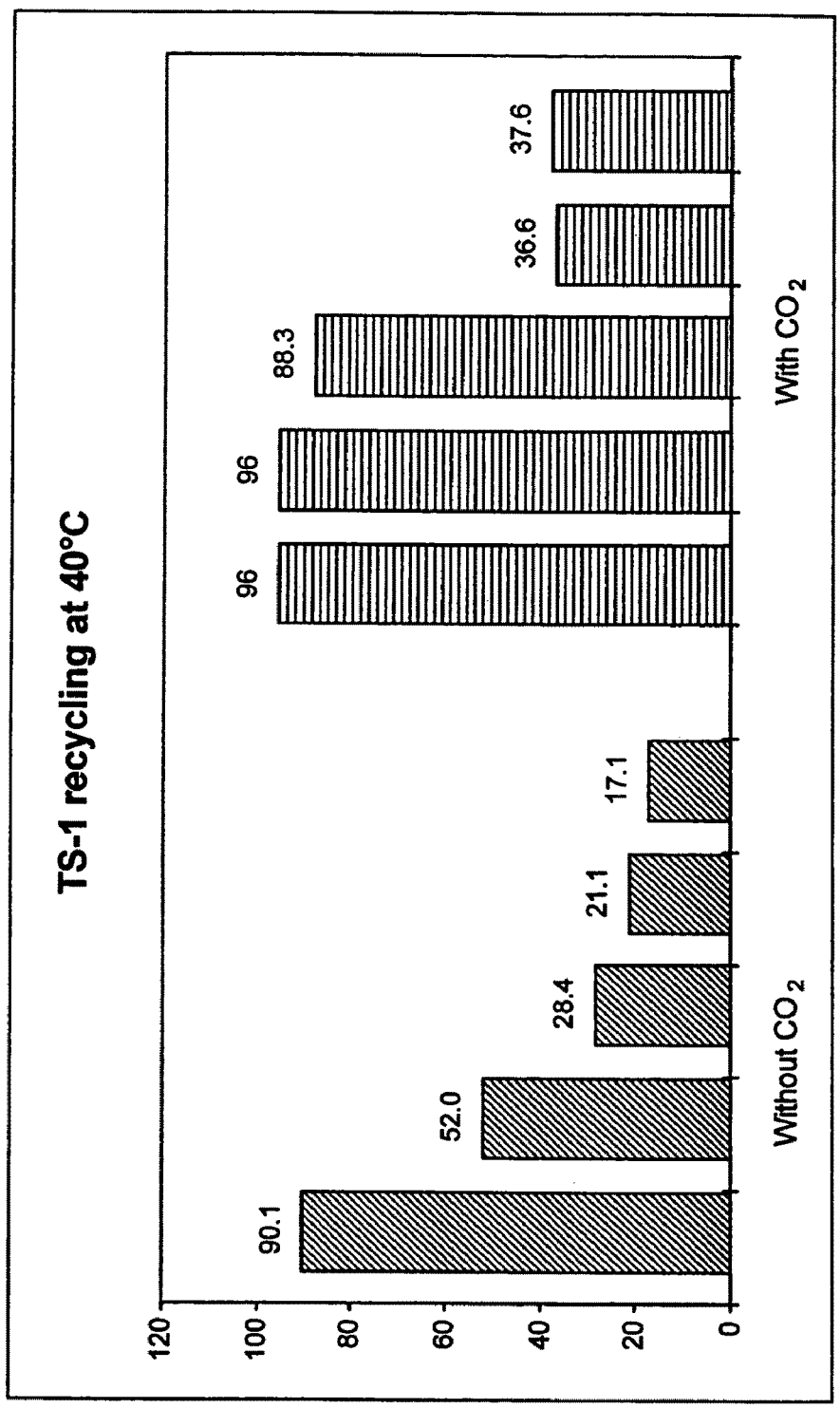
FIG. 1 is a graph of $H_2O_2$ conversion with and without $CO_2$ for TS-1 recycling at 40° C.

Accordingly the present invention provides a process for the conversion of one or more unsaturated hydrocarbons to one or more oxidation products which process comprises reacting one or more unsaturated hydrocarbons in a reaction mixture under oxidation conditions in the presence of an oxidant, heterogeneous catalyst and a solvent characterised in that the catalyst comprises a Group IVB, VB or VIB metal and that carbon dioxide is present in the reaction mixture.

In a preferred embodiment, the present invention pertains to an epoxidation process wherein a titanium containing catalyst is utilised in the presence of hydrogen peroxide as oxidant and the carbon dioxide is present in the reaction mixture under supercritical conditions.

Suitable oxidants for the process of the present invention may be hydrogen peroxide or hydroperoxides. Examples of hydroperoxides include tert-butyl hydroperoxide (TBHP) and ethyl benzene hydroperoxide (EBHP). The preferred oxidant for the process of the present invention is hydrogen peroxide ($H_2O_2$). Hydrogen peroxide ($H_2O_2$) utilised as the oxidant in the present invention may be obtained from any suitable source, including, for example, from autoxidation of secondary alcohols using air or other source of molecular oxygen. Suitable secondary alcohols include both aliphatic alcohols such as isopropanol and cyclohexanol as well as aromatic alcohols such as alpha methyl benzyl alcohol and anthrahydroquinones (including alkyl-substituted anthrahydroquinones). The crude reaction product thereby generated may be either used directly in the epoxidation process of this invention or, if so desired, purified, fractionated, concentrated, ion exchanged, or otherwise processed prior to such use. For example, the ketone generated as an autoxidation co-product may be separated, in whole or in part, from the hydrogen peroxide by distillation (where the ketone is relatively volatile) or by extraction with water (where the ketone is substantially immiscible with or insoluble in water). The hydrogen peroxide may alternatively be generated in situ by, for example, combining oxygen, secondary alcohol, olefin, and catalyst within a reaction zone under conditions effective to accomplish simultaneous secondary alcohol autoxidation and olefin epoxidation. Generally speaking, it will be desirable to employ initial hydrogen peroxide concentrations of from about 1 to 20 weight percent in the liquid phase within the reaction zone.

The unsaturated hydrocarbon is preferably an organic compound having from two to thirty carbon atoms and at least one ethylenically unsaturated functional group (i.e. a carbon-carbon double bond) and may be a cyclic, branched or straight chain aliphatic olefin. More than one carbon-carbon double bond may be present in the olefin, dienes, trienes, and other polyunsaturated substrates thus may be used.

Exemplary olefins suitable for use in the process of this invention include ethylene, propylene, the butenes, butadiene, the pentenes, isoprene, hexenes, heptenes, octenes, diisobutylene, nonenes, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene. Preferred olefins are 1-octene, propylene and cyclopentene.

Mixtures of olefins may be epoxidized and resulting mixture of epoxides either employed in mixed form or separated into the different component epoxides. One example of a preferred olefin mixture is a raffinate mixture which comprises mixed butenes; 1-butene, cis-2-butene, trans-2-butene and iso-butene.

The resulting epoxide or epoxide mixture may be rearranged to the corresponding linear aldehyde or ketone, either in-situ or in a separate step. Subsequent oxidation or hydrogenation of the aldehyde will result in the corresponding linear acid or linear alcohol. Subsequent hydrogenation of the ketone will result in secondary alcohols.

The process of this invention is especially useful for the epoxidation of $C_2$-$C_{10}$ olefins having the general structure:

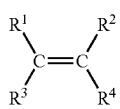

wherein $R^1$, $R^2$, $R^3$, and $R^4$ are the same or different and are selected from the group consisting of hydrogen and $C_1$-$C_8$ alkyl (selected so that the total number of carbons in the olefin does not exceed 30).

The process of this invention is also suitable for use in epoxidizing olefins containing functional groups other than aliphatic hydrocarbyl moieties. For example, the carbon-carbon double bond can be substituted with groups such as —$CO_2H$, —$CO_2R_1$, —CN, or —OR wherein R is an alkyl, cycloalkyl, aryl or aralkyl substituent. The radicals $R^1$, $R^2$, $R^3$, and $R^4$ in the structural formula shown hereinabove may contain aryl, aralkyl, halo, nitro, sulfonic, cyano, carbonyl, (e.g. ketone, aldehyde,) hydroxyl, carboxyl (e.g ester, acid) or ether groups. Examples of olefins of these types include allyl alcohol, styrene, allyl chloride, allyl methyl ether, allyl phenyl ether, methyl methacrylate, acrylic acid, methyl acrylate, and stilbene.

The amount of hydrogen peroxide relative to the amount of olefin is not critical, but most suitably the molar ratio of olefin:hydrogen peroxide is from about 100:1 to 1:10 when the olefin contains one ethylenically unsaturated group. The molar ratio of ethylenically unsaturated groups in the olefin to hydrogen peroxide is more preferably in the range of from 1:2 to 10:1.

The heterogeneous catalysts contain a Group IVB (e.g. Ti, Zr or Hf), VB (e.g. V, Nb or Ta) or VIB (e.g. Cr, Mo or W) metal and may be crystalline and/or amorphous. The most preferred catalysts contain a Group IVB metal. Particularly preferred catalysts are crystalline molecular sieves especially zeolites which contain titanium.

The titanium silicalites useful as catalysts in the epoxidation step of the process comprise the class of zeolite substances wherein titanium is substituted for a portion of the silicon atoms in the lattice framework of a molecular sieve. Such substances are well-known in the art.

Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable are the titanium-containing molecular sieves having framework structures isomorphous to zeolite beta. Also suitable is TS-48 with the structure of zeolite ZSM-48 as well as titanium mordenite with the MOR structure. The titanium silicalite preferably contains no non-oxygen elements other than titanium and silica in the lattice framework, although minor amounts of boron, iron, and aluminum may be present.

Titanium silicalite catalysts suitable for use in the process of this invention will generally have a composition corresponding to the following empirical formula $xTiO_2$: $(1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of relatively titanium-rich silicalites may also be desirable. The preferred catalyst is titanium silicalite-1. One form of catalyst suitable for use in the process of the present invention is a "cherry type" catalyst which consists of a core of material e.g. silica/alumina and a shell of different material e.g. silica/titania as described for example in EP 634 212. The titanium silicalite catalyst may be incorporated in or in the form of a membrane; for example TS-1 or Ti-MCM-41 may be occluded in polydimethylsiloxane (PDMS) membranes, as described in Chemical Communications (1997) pages 137 to 138.

The amount of catalyst employed is not critical, but should be sufficient so as to substantially accomplish the desired epoxidation reaction in a particularly short period of time. The optimum quantity of catalyst will depend upon a number of factors including reaction temperature, olefin reactivity and concentration, hydrogen peroxide concentration, type and concentration of organic solvent as well as catalyst activity and the type of reactor or reaction system (i.e. batch vs continuous) employed. In a batch-type or slurry reaction, for example, the amount of catalyst will typically be from 0.001 to 10 grams per mole of olefin. In a fixed or packed bed system, the optimum quantity of catalyst will be influenced by the flow rate of reactants through the fixed bed; typically, from about 0.05 to 2.0 kilograms hydrogen peroxide per kilogram catalyst per hour will be utilised. The concentration of titanium in the liquid phase reaction mixture will generally be from about 10 to 10,000 ppm.

The catalyst may be utilised in powder, pellet, microspheric, extruded, monolithic or any other suitable physical form. The use of a binder (co-gel) or support in combination with the titanium silicalite may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide. Two or more heterogeneous catalysts may be used if desired.

Illustrative binders and supports include titania, silica, alumina, silica-alumina, silica-titania, silica-thoria, silica-magnesia, silica-zirconia, silica-beryllia, and ternary compositions of silica with other refractory oxides. Also useful are clays such as montmorillonites, koalins, bentonites, halloysites, dickites, nacrites, and ananxites. The proportion of titanium silicalite binder or support may range from 99:1 to 1:99, but preferably is from 5:95 to 80:20.

The epoxidation reaction temperature is preferably from 0° C. to 100° C. (more preferably from 40° C. to 80° C.), which has been found to be sufficient to accomplish selective conversion of the olefin to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with high selectivities. The optimum reaction temperature will be influenced by catalyst concentration and activity, substrate reactivity, reactant concentrations and type of solvent employed, amongst other factors.

Reaction or residence times of from about 10 minutes to 48 hours will typically be appropriate, depending upon the above-identified variables. One advantage of the present invention however is that the reaction time required to achieve near quantitative conversion of the oxidant may be considerably shorter compared with those reactions undertaken in the absence of $CO_2$. This reduction in reaction time may be as much as 20% or even 50% or more. Thus the reaction residence time is at least 20% less and more preferably at least 50% less, than that required for 50%, more preferably 90% and most preferably 99% conversion of the oxidant, in a reaction without the presence of carbon dioxide.

The reaction is performed at elevated pressure (typically, between 1 and 700 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase is preferably utilised.

The epoxidation process of this invention may be manner using any appropriate type of reaction vessel or apparatus such as a fixed bed, transport bed, stirred slurry, or CSTR reactor. Known methods of conducting metal-catalysed epoxidations using hydrogen peroxide will generally also be suitable for use. Thus, the reactants may be combined all at once or sequentially. For example, the hydrogen peroxide and/or the olefin may be added incrementally to the reaction zone.

The oxidation must be carried out in the presence of carbon dioxide in the gaseous, liquid or supercritical state. It is most preferred that the carbon dioxide is present in the supercritical state which is where it exists as a one phase fluid occurring above both a critical temperature and pressure Tc and Pc, which is 31° C. and 73.8 kg/cm². The reaction mixture including catalyst comprises at least 1% by weight of carbon dioxide, preferably at least 10% by weight and more preferably at least 25% by weight of the reaction mixture including catalyst. In a most preferred embodiment the carbon dioxide constitutes more than 50% by weight of the solvent used in the reaction mixture.

Any solvent or combination of solvents which are compatible with carbon dioxide may be used. The preferred solvent has methanol as its main constituent in combination with carbon dioxide. Other suitable solvents include, but are not limited to water alcohols (especially $C_1$-$C_{10}$ aliphatic alcohols such as isopropanol), ketones (especially $C_3$-$C_{10}$ ketones such as acetone), and mixtures of such solvents. It is preferred that supercritical carbon dioxide is present as the solvent or in admixture with other solvents. Accordingly carbon dioxide when present as a solvent should be at least 1% by weight of the solvent mixture and preferably at least 5 to 100%, most preferably 25 to 100% by weight of the solvent. In a most preferred embodiment the carbon dioxide comprises at least 50% by weight of the solvent. The total amount of solvent in the reaction mixture will depend on a number of factors including the nature of the substrate being oxidised, the form and nature of introduction of the oxidant and the amount of $CO_2$ present. It has surprisingly been found that in the process of the present invention the ratio of solvent to substrate (unsaturated hydrocarbon or hydrocarbons being oxidised) may be significantly less than that required using the typical reaction conditions described in the art. This has the benefit of either enabling the reactor capacity to be better utilised or to enable the economic use of smaller reactors. In addition the requirement for less solvent results in less solvent recycle and a more energy efficient process. Typically reaction conditions in the art require solvent to substrate ratios of 8:1 or more. In the process of the present invention it is possible to use solvent to substrate ratios of less than 8:1 preferably 7:1 or less and most preferably 4:1 or less or 2:1 or less. Solvent to substrate ratios as low as 1:1 may be used; accordingly it is preferred that the ratio is within the range of 8:1 to 1:1 and most preferably 7:1 to 1:1 or narrower ranges based on the upper limits identified. Reduction of the ratio, when using the typical reaction conditions in the art, results in inefficient utilisation of the oxidant due to unwanted side reactions. In the process of the present invention the reduction in the ratio does not have a marked detrimental effect on oxidant efficiency which is significantly maintained at even the lowest ratios.

Once the epoxidation has been carried out to the desired degree of conversion, the epoxide product may be separated and recovered from the reaction mixture using any appropriate technique such as fractional distillation, extractive distillation, liquid-liquid extraction, or crystallisation. After separating from the epoxidation reaction mixture by any suitable method such as filtration (as when a slurry reactor is utilised, for example), the recovered titanium silicalite catalyst may be economically re-used in subsequent epoxidations. Where the catalyst is deployed in the form of a fixed bed, the epoxidation product withdrawn as a stream from the epoxidation zone will be essentially catalyst free with the catalyst being retained within the epoxidation zone. Similarly, any unreacted olefin or hydrogen peroxide may be separated and recycled or otherwise disposed of. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment. Such regeneration and/or treatment may not be necessary until a significant number of recycles have occurred through the process of the present invention. Typical examples of suitable regeneration methods are provided in WO99/01445, WO98/18556, WO98/28072 and Journal of Molecular Catalysis A: Chemical 117 (1997) 351-356. The disclosures of each of these references are incorporated by reference.

The present invention is further illustrated by means of the following examples:

Example 1

A TS-1 catalyst (prepared by the procedure given in Applied Catalysis, 99, (1993), pages 71-84) was utilised in the oxidation of 1-octene to 1,2-epoxyoctane with and without supercritical carbon dioxide as the solvent. A 250 cm$^3$ batch autoclave equipped with a temperature controller, mechanical stirrer (1000 rpm), reagents feed line, sampling line and vent line was charged in two separate experiments with the following reagents.

| Reagents | Experiment 1 Weight (g) | Experiment 2 Weight (g) |
| --- | --- | --- |
| 1-octene | 14.52 | 7.26 |
| $H_2O_2$ (30 wt % in $H_2O$) | 0.44* | 0.22* |
| Methanol | 112.5 | 56.25 |
| Carbon Dioxide | 0 | 74.2 |
| TS-1 catalyst | 1.0 | 0.5 |
| Total | 128.46 | 138.43 |

*= the weight of $H_2O_2$ does not include the weight of H20

For Experiment 1 the reaction was undertaken at 65° C. for 60 minutes. For Experiment 2 the reactor was first pressurised with carbon dioxide gas to 48 bar ($48 \times 10^5$ Nm$^{-2}$), after which 74.2 g of liquid carbon dioxide was added. The reaction was undertaken at 65° C. for 60 minutes and at a pressure of 106 bar ($106 \times 10^5$ Nm$^{-2}$) The composition of the reaction mixtures was determined using Gas Chromatography and the hydrogen peroxide content was determined using iodometric titration.

The results are provided in Table 1.

TABLE 1

| Experiment | Mole % 1,2-epoxyoctane | Mole % Glycolethers | % Conversion of $H_2O_2$ |
| --- | --- | --- | --- |
| 1 | 77.8 | 22.2 | 97.9 |
| 2 | 91.1 | 8.9 | 98 |

It can be seen from the above results that for a given conversion the selectivity is greatly enhanced when carbon dioxide is used in the oxidation utilising TS-1 as catalyst.

Example 2

In a further set of experiments the solvent system utilised was methanol or methanol/$CO_2$ under supercritical conditions.

In a first set of experiments (Experiment 3) the TS-1 catalyst was used in a methanol solvent and recycled without treatment or regeneration. In a second set of experiments (Experiment 4) the TS-1 catalyst was used in a methanol/carbon dioxide solvent system under supercritical conditions with respect to the carbon dioxide again the catalyst was recycled without further treatment or regeneration.

Methanol Solvent—Catalyst Recycle

The following reagents were used:

| Reagents | Experiment 3 Weight (g) |
| --- | --- |
| 1-octene | 7.26 |
| $H_2O_2$ (30 wt % in $H_2O$) | 0.22* |
| Methanol | 56.3 |
| Carbon Dioxide | 0 |
| TS-1 catalyst | 0.5 |
| Total | 64.23 |

*= the weight of $H_2O_2$ does not include the weight of $H_2O$

The reaction was undertaken at 40° C. for 60 minutes in a 100 cm$^3$ glass reactor with magnetic stirrer and chilled water cooler on an electrical heating mantle. On completion the reactor was recharged with reagents and the used catalyst was recycled by filtration and drying in vacuo at room temperature for 10 minutes. The catalyst was recycled four times and the results are provided in Table 2.

TABLE 2

| Run Number | Mole % 1,2-epoxyoctane | Mole % Glycolethers | % Conversion of $H_2O_2$ |
| --- | --- | --- | --- |
| 1. Fresh catalyst | 89.5 | 10.5 | 90.1 |
| 2. First recycle | 100 | 0 | 52.0 |
| 3. Second recycle | 100 | 0 | 28.4 |
| 4. Third recycle | 100 | 0 | 21.1 |
| 5. Fourth recycle | 100 | 0 | 17.1 |

It can be seen from the results in Table 2 that the conversion of hydrogen peroxide is dramatically reduced on recycling the catalyst.

Methanol Solvent with Carbon Dioxide—Catalyst Recycle

The following reagents were used:

| Reagents | Experiment 4 Weight (g) |
| --- | --- |
| 1-octene | 7.26 |
| $H_2O_2$ (30 wt % in $H_2O$) | 0.22* |
| Methanol | 56.25 |
| Carbon Dioxide | 82.8 |
| TS-1 catalyst | 0.5 |
| Total | 147.03 |

*= the weight of $H_2O_2$ does not include the weight of $H_2O$

A 250 cm$^3$ batch autoclave equipped with a temperature controller, mechanical stirrer, reagents feed line, sampling line and vent line was filled with all the above reagents except carbon dioxide and 1-octene. Then the reactor was pressurised with carbon dioxide gas to 52 bar ($52 \times 10^5$ Nm$^{-2}$), after which 82.6 g of liquid carbon dioxide was added, then 1-octene was injected and the reaction was undertaken at 40° C. for 30 minutes and at a pressure of 74.3 bar ($74.3 \times 10^5$ Nm$^{-2}$). On completion of the reaction the catalyst was removed by filtration and dried in air before being twice recycled using the same reactor, reagents and conditions. The results are provided in Table 3.

TABLE 3

| Run Number | Mole % 1,2-epoxyoctane | Mole % Glycolether | % Conversion of $H_2O_2$ |
|---|---|---|---|
| 1. Fresh catalyst | 100 | 0 | 96 |
| 2. First recycle | 100 | 0 | 96 |
| 3. Second recycle | 100 | 0 | 88 |
| 4. Third recycle | 100 | 0 | 36.6 |
| 5. Fifth recycle | 100 | 0 | 37.6 |

Figure 2:
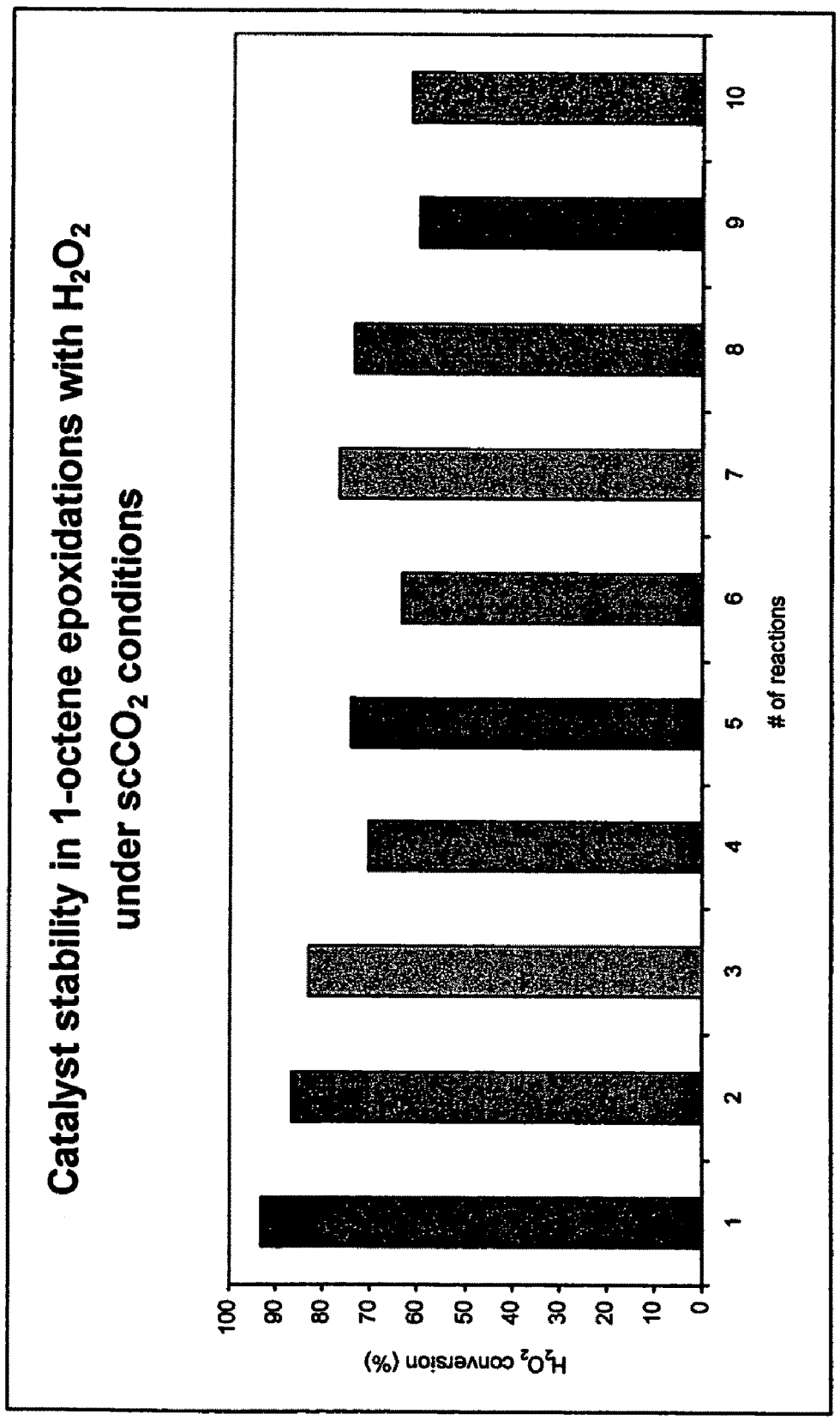
FIG. 2 is a graph of $H_2O_2$ conversion versus number of reactions reflecting catalyst stability in 1-octene epoxidation with $H_2O_2$ under sc$CO_2$ conditions.
Figure 3:
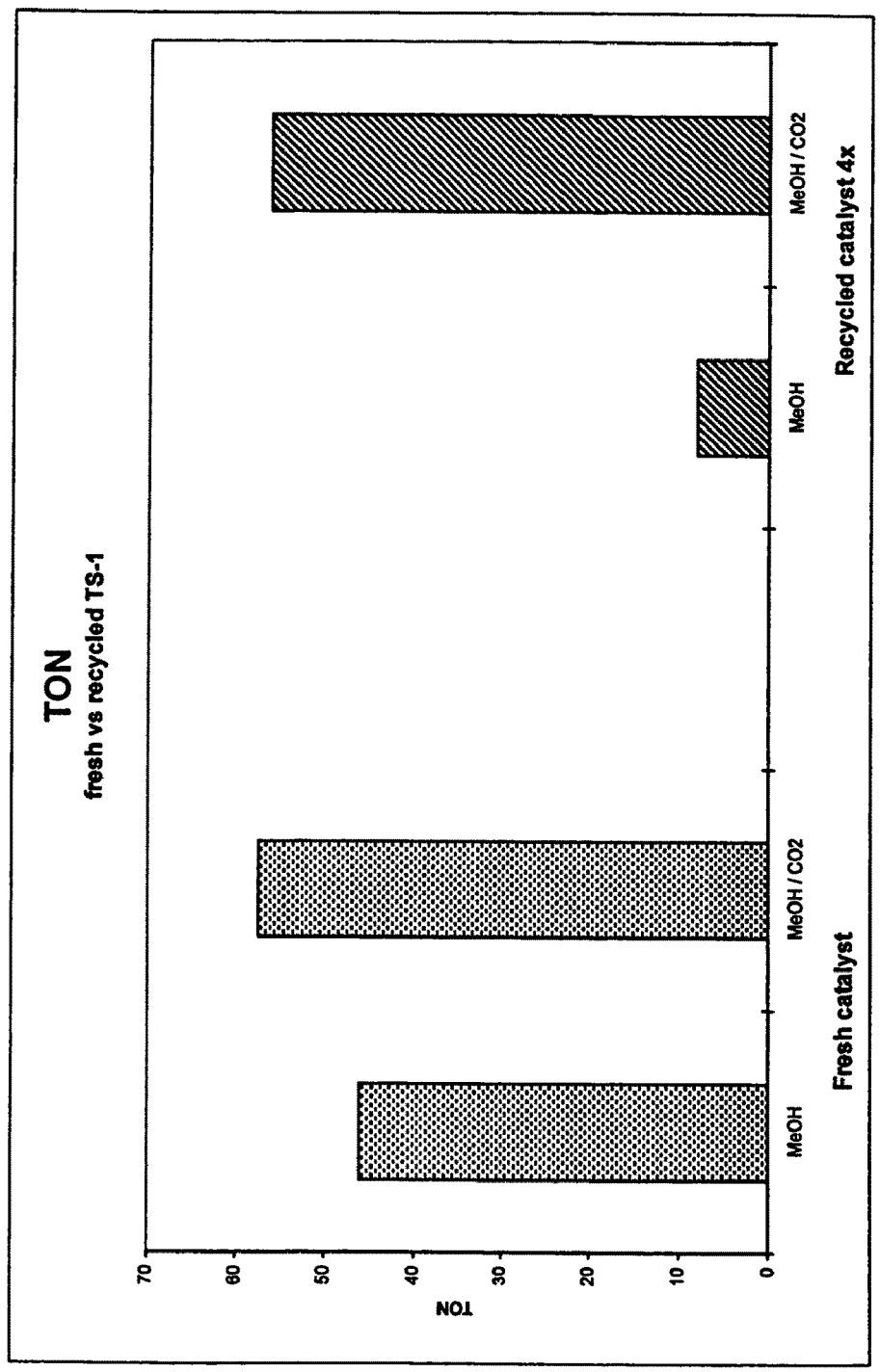
FIG. 3 is a graph of turnover number (TON) in fresh and recycled catalyst.

It can be seen from the results in Table 3 that utilising carbon dioxide in the reaction enables the catalyst to be recycled without a dramatic reduction in hydrogen peroxide conversion whilst maintaining a high selectivity towards the desired epoxide. The results are illustrated in FIG. 1, which shows the % conversion for each recycle. FIG. 2 illustrates the stability of a catalyst in pellet form, over 10 reaction recycles, under the process conditions of experiment 4 of this example. Between 70 to 80% of the original catalyst weight was recovered at the end of the recycle. Some of the reduced conversion identified in FIGS. 1 and 2 is not due to catalyst deactivation but is due to catalyst losses from the reactor. FIG. 3 illustrates the conversion with and without carbon dioxide using turn-over number (TON). Turnover number corrects for the effects of catalyst losses from the reactor between reaction cycles and is a calculated as follows for each reaction period:

TON=mmol of epoxide/mmol of titanium in the catalyst

The results in FIG. 3 show that when methanol is used as the solvent there is a dramatic reduction in catalyst effectiveness after four reaction cycles whereas when carbon dioxide is utilised according to the invention there is no significant reduction in catalyst activity after the same number of cycles.

Example 3

Figure 4:
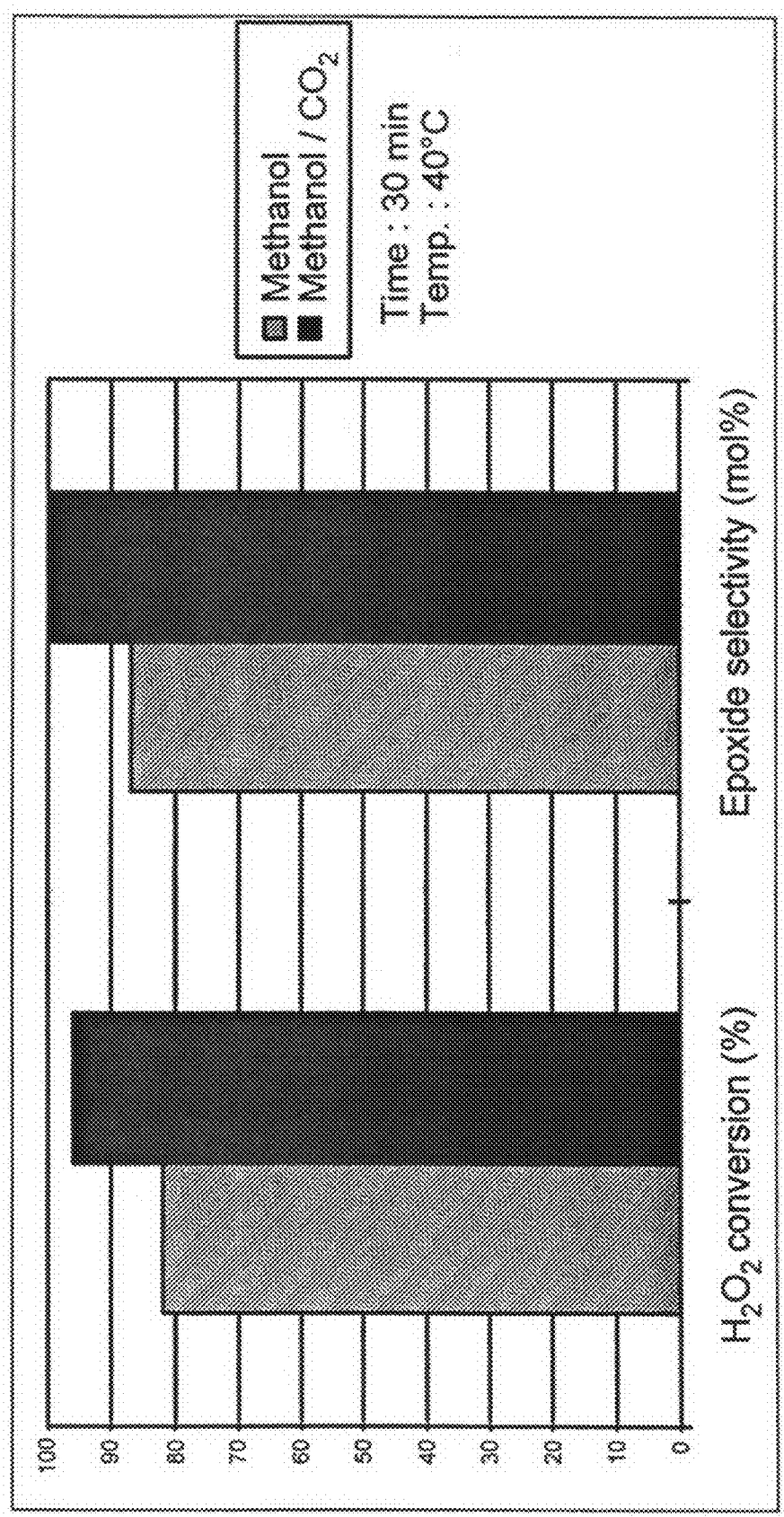
FIG. 4 is a graph of $H_2O_2$ conversion and epoxide selectivity comparing methanol with and methanol and $CO_2$.

Example 1 was repeated with the exception that the reaction time was 30 minutes and the reaction temperature was 40° C. The results are provided in FIG. 4; these results illustrate that at short reaction times and low temperature the process of the invention provides improved selectivity and oxidant conversion.

Example 4

The general procedure of example 1 experiment 2 was repeated using a raffinate-2 feedstock in place of the 1-octene. The raffinate-2 feedstock comprised 29.9 wt % of 1-butene, 21.6 wt % of cis-2-butene, 36.8 wt % of trans-2-butene and 1.9 wt % of iso-butene.

In the reaction the following proportions and conditions were used: 3.6 g (58.3 mmol) of butenes; 0.656 g (5.8 mmol) of $H_2O_2$ (as a 30% solution in $H_2O$); 0.5 g of TS-1 pellets; 50 g methanol; and a $CO_2$ pressure of 89 bar for 1 hour at 40° C.

The reaction resulted in 98.2% selectivity for the epoxides compared with a selectivity of 93% without the use of carbon dioxide.

Example 5

The general procedure of example 1 was repeated using a cyclopentene feedstock in place of the 1-octene.

In the reaction the following proportions and conditions were used: 3.93 g (58.3 mmol) of cyclopentene, 0.656 g (5.8 mmol) of $H_2O_2$ (as a 30% solution in $H_2O$), 0.5 g of TS-1 pellets, 50 g methanol and a $CO_2$ pressure of 88 bar for 1 hour at 40° C.

The reaction resulted in 94% selectivity for the epoxide compared with a selectivity of 59% without the use of carbon dioxide.

Example 6

The general procedure of example 1 was repeated using a propylene feedstock in place of the 1-octene In the reaction the following proportions and conditions were used: 2.47 g (58.3 mmol) of propylene, 0.656 g (5.8 mmol) of $H_2O_2$ (as a 30% solution in $H_2O$), 0.5 g of TS-1 pellets, 50 g methanol and a $CO_2$ pressure of 88 bar for 1 hour at 40° C.

The reaction resulted in 100% selectivity for the epoxide compared with a selectivity of 87% without the use of carbon dioxide.

Example 7

Figure 5:
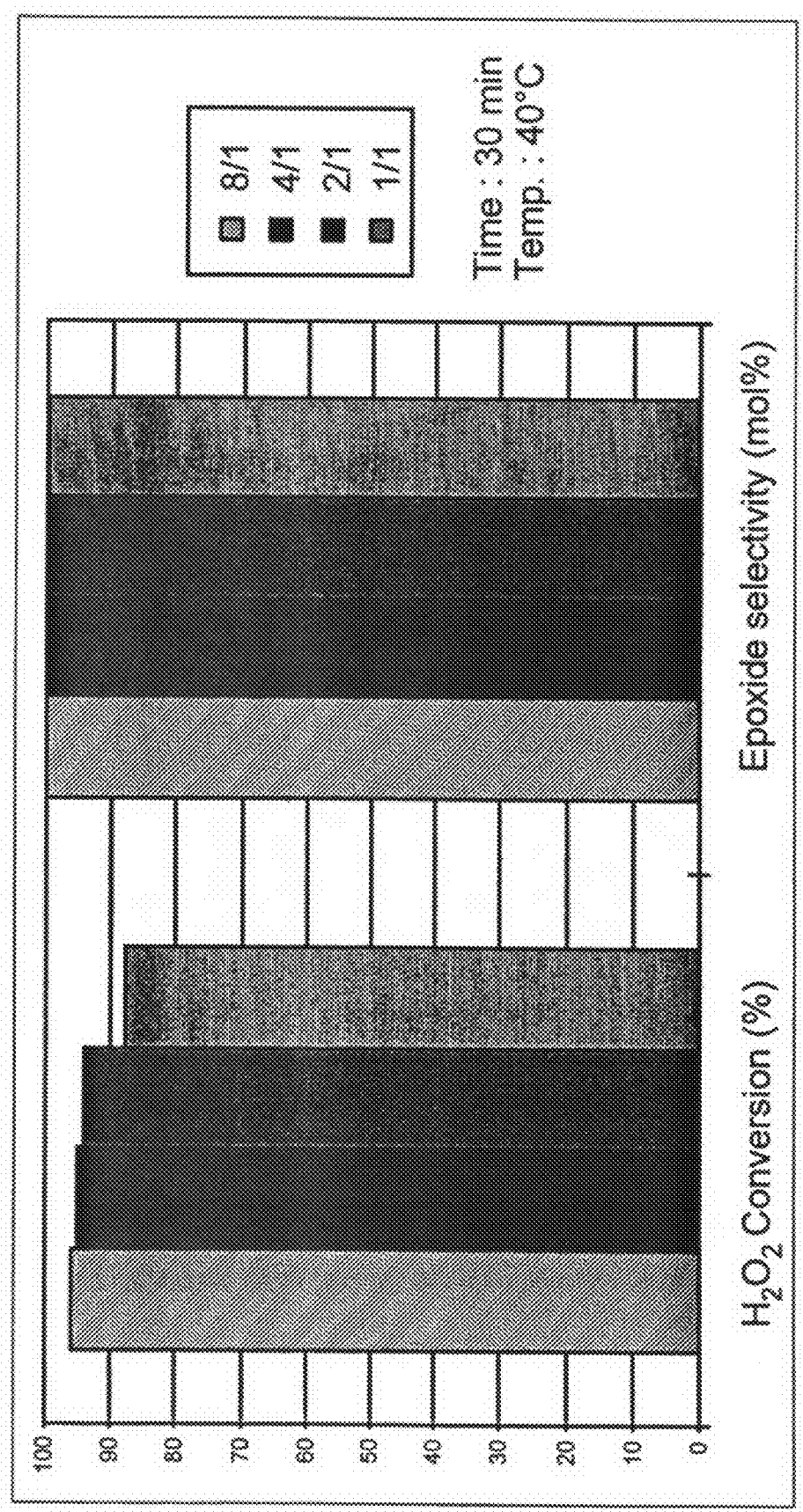
FIG. 5 is a graph of $H_2O_2$ conversion and epoxide selectivity at different ratios of solvent to substrate.

A series of experiments were undertaken using the general procedure of Example 3 at 40° C. for 30 minutes, with the exception that for some of the experiments the solvent to 1-octene ratio was decreased. The results are illustrated in FIG. 5. These results show that even at low ratios of solvent to substrate the epoxide selectivity and oxidant conversion both remain high.

The invention claimed is:

1. A process for the conversion of one or more unsaturated hydrocarbons to one or more epoxides which process comprises reacting one or more unsaturated hydrocarbons in a reaction mixture under oxidation conditions in the presence of an oxidant, a heterogeneous catalyst and a solvent characterized in that the catalyst comprises a metal selected from the group consisting of Ti, Zr, Hf, V, Nb, Ta, Cr, Mo and W, and that carbon dioxide is present in the reaction mixture under supercritical conditions and wherein the reaction mixture comprises at least 1% by weight of the carbon dioxide.

2. The process of claim 1 wherein the catalyst is a metal molecular sieve.

3. The process of claim 1 wherein the metal is Ti, Zr or Hf.

4. The process of claim 3 wherein the metal is titanium.

5. The process of claim 1 wherein the solvent is methanol.

6. The process of claim 1 wherein the oxidant is hydrogen peroxide.

7. The process of claim 1 wherein the unsaturated hydrocarbon is an olefin.

8. The process of claim 7 wherein the carbon dioxide constitutes more than 50% by weight of the solvent used in the reaction mixture.

9. The process of claim 1 wherein the ratio of solvent to unsaturated hydrocarbon is less than 8:1.

10. The process of claim 9 wherein the ratio is 1:1 or less.

11. The process of claim 1 wherein the reaction mixture comprises at least 25% by weight of carbon dioxide.

12. The process of claim 1 wherein the carbon dioxide constitutes more than 50% by weight of the solvent used in the reaction mixture.

13. The process of claim 1 wherein the catalyst is selected from one of the following: TS-1, TS-2, TS-3, titanium zeolite beta, TS-48, titanium mordenite and titanium silicalite.

14. The process of claim 1 wherein the reaction residence time is at least 20% less than that required to achieve 50% conversion without the presence of carbon dioxide.

15. The process of claim 14 wherein the reaction residence time is at least 50% less.

16. The process of claim 15 wherein the conversion is 90%.

17. The process of claim 1 wherein the reaction pressure is between 1 and 700 atmospheres.

18. The process of claim 1 wherein the reaction temperature is from 0° C. to 100° C.

19. The process of claim 18 wherein the reaction temperature is within the range 40° C. to 80° C.

20. The process of claim 1 wherein the reaction residence time is within the range of 10 minutes to 48 hours.

21. A process for the conversion of one or more olefins selected from the group consisting of ethylene, propylene, the butenes, butadiene, the pentenes, isoprene, hexenes, heptenes, octenes, diisobutylene, nonenes, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene, to one or more epoxides which process comprises reacting one or more unsaturated hydrocarbons in a reaction mixture under oxidation conditions in the presence of an oxidant, a heterogeneous catalyst and a solvent characterized in that the catalyst comprises a metal selected from the group consisting of Ti, Zr, Hf, V, Nb, Ta, Cr, Mo and W, and that carbon dioxide is present in the reaction mixture under supercritical conditions and wherein the reaction mixture comprises at least 1% by weight of the carbon dioxide.

22. The process of claim 21 wherein the catalyst is a molecular sieve containing Ti, Zr or Hf.

23. The process of claim 22 wherein the metal is titanium.

24. A process for the conversion of one or more unsaturated hydrocarbons to one or more epoxides which process comprises reacting one or more unsaturated hydrocarbons in a reaction mixture under oxidation conditions in the presence of an oxidant, a heterogeneous catalyst and a solvent characterized in that the catalyst is a molecular sieve containing Ti, and that carbon dioxide is present in the reaction mixture under supercritical conditions and wherein the reaction mixture comprises at least 1% by weight of the carbon dioxide and wherein the titanium is substituted for a portion of the silicon atoms in the lattice frame work of the molecular sieve.

25. The process of claim 21 wherein the solvent is methanol.

26. The process of claim 21 wherein the oxidant is hydrogen peroxide.

27. The process of claim 21 wherein the ratio of solvent to unsaturated hydrocarbon is less than 8:1.

28. The process of claim 21 wherein the reaction mixture comprises at least 25% by weight of carbon dioxide.

29. The process of claim 21 wherein the heterogeneous catalyst is selected from the group consisting of: TS-1, TS-2, TS-3, titanium zeolite beta, TS-48, titanium mordenite and titanium silicalite.

30. The process of claim 21 wherein the reaction residence time is at least 20% less than that required to achieve 50% conversion without the presence of carbon dioxide in the supercritical state.

31. The process of claim 21 wherein the reaction is run at a pressure between 1 and 700 atmospheres and/or at a temperature from 0° C. to 100° C.

32. The process of claim 21 wherein the reaction has a residence time of from 10 minutes to 48 hours.

33. A process for the conversion of one or more unsaturated olefins to one or more epoxides comprising reacting one or more unsaturated olefins in a reaction mixture under oxidation conditions comprising a pressure of between 1 and 700 atmospheres, a temperature from 1 to 100° C., and a residence time of 10 minutes to 48 hours in the presence of an oxidant, a heterogeneous catalyst comprising a molecular sieve where titanium is substituted for a portion of the silicon atoms in the lattice frame work of the molecular sieve, and a solvent, wherein carbon dioxide is present in the reaction mixture under supercritical conditions and the reaction mixture comprises at least 1% by weight of carbon dioxide.

34. The process of claim 33 wherein the heterogeneous catalyst is selected from the group consisting of: TS-1, TS-2, TS-3, titanium zeolite beta, TS-48, titanium mordenite and titanium silicalite.

35. The process of claim 33 wherein the solvent is methanol and/or the oxidant is hydrogen peroxide.

36. The process of claim 33 wherein the olefin is selected from the group consisting of ethylene, propylene, the butenes, butadiene, the pentenes, isoprene, hexenes, heptenes, octenes, diisobutylene, nonenes, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene.

37. The process of claim 33 wherein the olefin is selected from the group consisting of 1-octene, propylene and cyclopentene.

38. The process of claim 33 where the olefin is a mixture of olefins.

39. The process of claim 33 where the olefin is a raffinate mixture which comprises mixed butenes; 1-butene, cis-2butene, trans-2-butene and iso-butene.

\* \* \* \* \*